US006962561B2

United States Patent
Bruno et al.

(10) Patent No.: US 6,962,561 B2
(45) Date of Patent: *Nov. 8, 2005

(54) METHOD FOR BIOSOLID DISPOSAL AND METHANE GENERATION

(75) Inventors: Michael S. Bruno, Monrovia, CA (US); Maurice B. Dusseault, Osoyoos (CA); Roman Bilak, Calgary (CA)

(73) Assignees: Terralog Technologies USA, Inc., Arcadia, CA (US); Terralog Technologies Inc., Calgary (CA)

( * ) Notice: Subject to any disclaimer, the term of this patent is extended or adjusted under 35 U.S.C. 154(b) by 192 days.

This patent is subject to a terminal disclaimer.

(21) Appl. No.: 10/294,218

(22) Filed: Nov. 13, 2002

(65) Prior Publication Data

US 2003/0135083 A1 Jul. 17, 2003

Related U.S. Application Data

(63) Continuation-in-part of application No. 10/123,828, filed on Apr. 15, 2002, now Pat. No. 6,491,616, which is a continuation of application No. 09/917,417, filed on Jul. 27, 2001, now Pat. No. 6,409,650, which is a continuation-in-part of application No. 09/620,085, filed on Jul. 20, 2000, now Pat. No. 6,287,248.
(60) Provisional application No. 60/150,677, filed on Aug. 25, 1999.

(51) Int. Cl.⁷ .............................. A02D 3/00; B09B 3/00; E21B 43/00; E21B 47/06
(52) U.S. Cl. ................... 588/250; 166/246; 166/250.7; 166/302; 405/129.25; 405/129.35; 405/129.45; 588/205; 588/260
(58) Field of Search ............................. 166/246, 250.7, 166/302, 308.1, 308.2; 405/129.25, 129.35, 129.45; 435/262.5; 588/205, 250, 254, 258, 260

(56) References Cited

U.S. PATENT DOCUMENTS

| 3,335,798 | A | * | 8/1967 | Querin et al. ............ 166/305.1 |
| 5,202,522 | A | | 4/1993 | Williams |
| 5,484,231 | A | * | 1/1996 | Cannan et al. ........... 405/129.4 |
| 5,605,417 | A | | 2/1997 | Englert et al. |
| 5,821,113 | A | | 10/1998 | Haslimann |
| 6,002,063 | A | * | 12/1999 | Bilak et al. .................... 588/17 |
| 6,137,028 | A | * | 10/2000 | Snow ......................... 588/250 |
| 6,287,248 | B1 | * | 9/2001 | Bruno et al. ................ 588/250 |
| 6,409,650 | B2 | * | 6/2002 | Bruno et al. ................ 588/250 |
| 6,491,616 | B2 | * | 12/2002 | Bruno et al. ................ 588/250 |

FOREIGN PATENT DOCUMENTS

| CA | 2185259 | 12/1997 |
| GB | 2161015 | 1/1986 |

OTHER PUBLICATIONS

Dusseault, Maurice B. et al, "Disposal of Radioactive Wastes by Slurry Fracture Injection", Conference Paper (Sep. 1996).*

Dusseault M. B.: Slurry Injection Disposal of Granular Solid Waste Stockage Permanent. Geoconfine. 1993 pp. 511–517.

* cited by examiner

*Primary Examiner*—George Suchfield
(74) *Attorney, Agent, or Firm*—David A. Farah; Sheldon & Mak PC

(57) ABSTRACT

A method for the disposal of biosolids, the method comprising providing a supply of biosolids; selecting an introduction formation below a ground surface, the introduction formation comprising a natural gas formation in a gas accumulation zone; introducing the biosolids into the introduction formation at a pressure sufficient to create and maintain fractures within the selected introduction formation; and allowing degradation of the introduced biosolids.

21 Claims, 1 Drawing Sheet

METHOD FOR BIOSOLID DISPOSAL AND METHANE GENERATION

CROSS-REFERENCE TO RELATED APPLICATION

Figure 1:
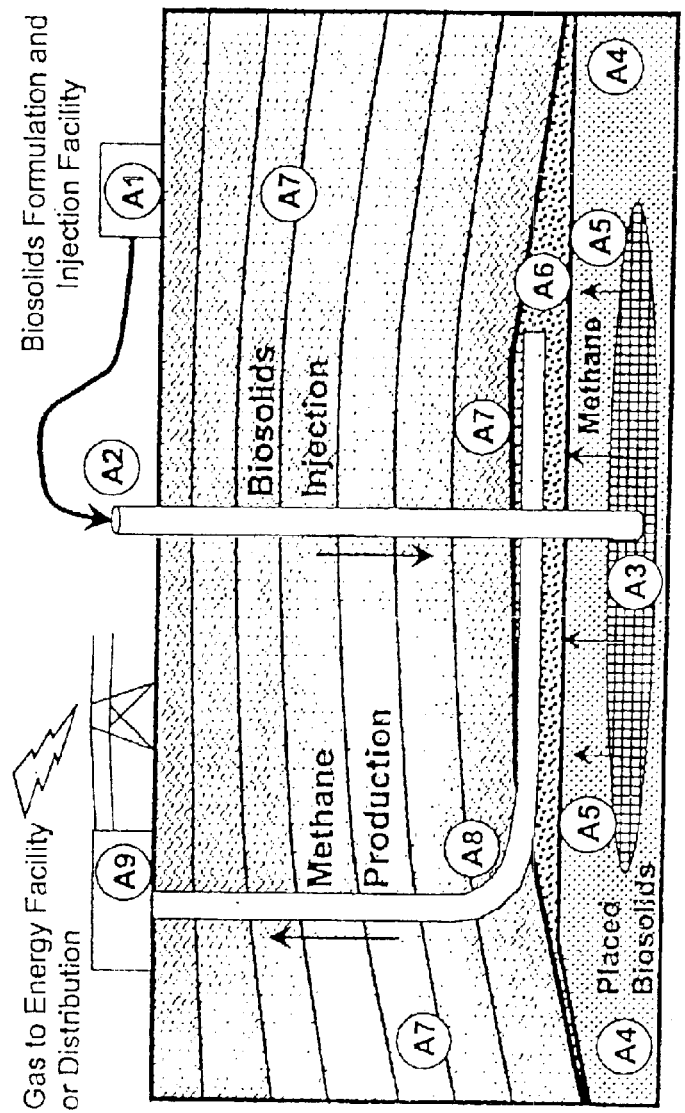

This application is a continuation-in-part of U.S. patent application Ser. No. 10/123,828 titled "Method for Biosolid Disposal and Methane Generation" filed Apr. 15, 2002, now U.S. Pat. No. 6,491,616 which is a continuation of U.S. patent application Ser. No. 09/917,417 titled "Method for Biosolid Disposal and Methane Generation" filed Jul. 27, 2001, now U.S. Pat. No. 6,409,650 B1, issued Jun. 25, 2002; which is a continuation-in-part of U.S. patent application Ser. No. 09/620,085 titled "Method for Biosolid Disposal and Methane Generation," filed Jul. 20, 2000, now U.S. Pat. No. 6,287,248, issued Sep. 11, 2001; and claims the benefit of U.S. provisional patent application No. 60/150,677 titled "Method for Municipal Waste Disposal and Recovery of Byproducts," filed Aug. 25, 1999; the contents of each of which are hereby incorporated herein by reference in their entirety.

BACKGROUND

Over 10 million tons of biosolids from municipal sewage sludge are generated each year in the United States alone. The prevailing methods for the disposal of biosolids include the application of the biosolids to surface land application, such as to crop land, range land or forests, composting and landfill disposal. Each of these methods is associated with disadvantages.

For example, one disadvantage of the application of biosolids to surface lands is the resistance of persons living in the area of the application because of concerns about nuisances such as odor and wind-blown dust from the site of application. Biosolids application to surface land and landfills also creates risks for contamination of potable surface water and groundwater.

Further, disadvantageous weather conditions can delay the application of biosolids to surface land, and trucking biosolids to the application site creates pollution and nuisances. Additionally, the capacity for the disposal of biosolids by application to surface lands and landfills is limited and the associated costs are generally high. Also, greenhouse gasses, such as methane and carbon dioxide, are generated by the decomposition of the biosolids and these gases are released into the atmosphere at the sites of surface land application and most landfills.

Therefore, there is a need for an additional method for the disposal of biosolids that provides less risk for environmental contamination. Additionally, there is a need for an additional method for the disposal of biosolids that is less expensive. Further, there is a need for an additional method for the disposal of biosolids that does not permit the release of carbon dioxide and other green house gases into the atmosphere. Also, there is a need for an additional method for the disposal of biosolids that can produce usable byproducts from biosolids.

SUMMARY

According to one embodiment of the present invention, there is provided a method for the disposal of biosolids. The method comprises, first, providing a supply of biosolids. The introduction formation comprises a natural gas formation in a gas accumulation zone. Next, the biosolids are introduced into the introduction formation at a pressure sufficient to create and maintain fractures within the selected introduction formation. Then, the introduced biosolids are allowed to degrade.

In a preferred embodiment, the supply of biosolids can be derived from at least one source selected from the group consisting of municipal sewage waste, waste water treatment waste, animal waste, non-human-non-animal industrial waste and a combination of the preceding. In another preferred embodiment, the introduction formation is at least about 100 meters below the ground surface. In a particularly preferred embodiment, the introduction formation is from between about 500 and about 3,000 meters below the ground surface.

In a preferred embodiment, the introduction formation has a temperature and the temperature of the introduction formation is greater that about 25° C. In another preferred embodiment, the introduction formation has a porosity greater than about 15%. In a particularly preferred embodiment, the introduction formation is separated from the ground surface by one or more pairs of alternating layers of high permeability and low permeability.

In a preferred embodiment, the method further comprises monitoring pressure in the one or more than one of the alternating layers of high permeability and low permeability above the introduction formation during a time selected from the group consisting of before biosolids introduction, during biosolids introduction, after biosolids introduction and a combination of before biosolids introduction, during biosolids introduction and after biosolids introduction. In a preferred embodiment, at least one low permeability layer of the one or more alternating layers of high permeability and low permeability comprises shale. In a particularly preferred embodiment, the one or more pairs of alternating layers of high permeability and low permeability is at least three pairs of alternating layers of high permeability and low permeability.

In a preferred embodiment, the degeneration of the biosolids generates a gas selected from the group consisting of carbon dioxide, sulfur dioxide, hydrogen sulfide and combinations of the preceding. In a particularly preferred embodiment, the method further comprises decreasing the rate of the generated carbon dioxide, sulfur dioxide, hydrogen sulfide or combination of the preceding by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding.

In a preferred embodiment, the method further comprises creating fractures within the introduction formation before injecting the biosolids into the introduction formation. In another preferred embodiment, the method further comprises transporting the selected biosolids to an introduction site by pipe before injecting the biosolids. In a particularly preferred embodiment, the method further comprises monitoring pressure in the introduction formation at a time selected from the group consisting of before injecting the biosolids into the introduction formation, during the introduction of the biosolids into the introduction formation, after injecting the biosolids into the introduction formation and a combination of the preceding.

In a preferred embodiment, the method further comprises increasing the rate of degradation of the biosolids by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding. In another preferred embodiment, the chemical added to the biosolids is potassium. In a particularly preferred embodiment, the method further comprises allowing methane to be generated by the degradation of the introduced biosolids and recovering methane generated by the degradation of the introduced biosolids, after injecting the biosolids into the introduction formation. In a particularly preferred embodiment, the rate of methane generation is increased by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding. In another preferred embodiment, the chemical added to the biosolids is potassium.

In a preferred embodiment, the degradation of the biosolids generates a gas selected from the group consisting of carbon dioxide, sulfur dioxide, hydrogen sulfide and combinations of the preceding, and where the method further comprises decreasing the rate of the generated carbon dioxide, sulfur dioxide, hydrogen sulfide or combination of the preceding by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding. In another preferred embodiment, the chemical added to the biosolids is potassium.

FIGURES

The features, aspects and advantages of the present invention will become better understood with regard to the following description, appended claims and accompanying figures where:

FIG. 1 is a schematic diagram of one embodiment of the method for the disposal of biosolids according to the present invention.

DESCRIPTION

In one embodiment, the present invention is a method for the disposal of solids, such as biosolids, comprising injecting the biosolids into deep underground formations. The introduced biosolids are then allowed to undergo biodegradation, using the natural geothermal heat in the deep subsurface. Biodegradation produces carbon dioxide, sulfur dioxide, hydrogen sulfide, methane and other gases. The generated carbon dioxide is absorbed by formation waters because it is highly soluble in water, and more soluble than methane. The residue from the biodegradation is a carbon-rich solid material that becomes permanently sequestered in the underground formation.

In a preferred embodiment, methane generated by the degrading biosolids is removed for conversion into usable energy, or storage for subsequent use. In another preferred embodiment, the rate of biodegradation is increased or the rate of methane production is increased or the rate of carbon dioxide or other undesirable degradation products is decreased by altering environmental conditions in the formation or by adding substances or bacteria, or by adjusting the biochemical properties of the biosolids that are introduced into the formation. The present method provides significant cost savings and environmental benefits over current technologies for the disposal of biosolids.

As used in this disclosure, the term "biosolids" is defined as solid particles of matter that are dominantly comprised of organic material by weight.

The method of the present invention will now be discussed in greater detail. First, a suitable supply of biosolids is provided. In a preferred embodiment, the biosolids have sufficient concentration of biodegradable organic matter to generate exploitable quantities of methane. It is not necessary that all the wastes be biodegradable or even organic as other solid components of the introduced biosolids will become permanently entombed in the introduction formation.

In a preferred embodiment, the biosolids disposed of by the present method will be derived from municipal sewage or waste water treatment wastes, such as produced by a major metropolitan area. Municipal sewage wastes comprise human biowastes, household scraps, sanitary paper products and other biological components, as well as mineral matter and small amounts of chemical products, such as solvents, acids, alkalies and heavy metals, introduced into the waste stream through the municipal sewer system such as solvents, acids, alkalies and heavy metals.

Another suitable source of the biosolids is animal wastes from sites where the animals are raised or housed. The animal wastes can be mixed with other organic materials such as sawdust or straw, or it may be mixed with mineral wastes. Still other suitable sources of biosolids are pulp and paper mill sludges, waste oil products including greases and waxes, and wastes which are rich in organic debris dredged from harbors or estuaries.

After providing a suitable supply of biosolids, a suitable underground formation, designated the "introduction formation" in this disclosure, is selected below a suitable ground surface introduction site. Preferably, the formation is a high porosity, high permeability sand formation, significantly below usable groundwater, if present. In a particularly preferred embodiment, the porosity is greater than about 15%. In a particularly preferred embodiment, the introduction formation is below any groundwater which could be removed for human use and below multiple, thick and clearly defined layers of alternating low permeability, fluid flow barriers and high permeability fluid absorption zones. The high permeability layers will preferably be sand of high porosity. The low permeability layers will preferably comprise shales and other rocks containing clay minerals that have absorptive capacity. In a preferred embodiment, there should be at least two alternating layers of high permeability and low permeability separating any usable groundwater, if present, and the deeper introduction formation. In a particularly preferred embodiment, there should be at least five alternating layers of high permeability and low permeability separating any usable groundwater, if present, and the deeper introduction formation.

The total available storage volume of an introduction formation can be calculated based on the approximate average thickness and area of the introduction formation, the average porosity of the introduction formation and the mechanical compressibility of the introduction formation, as will be understood by those with skill in the art with reference to this disclosure.

In another preferred embodiment, the introduction formation will be at least about 100 m below the ground surface. This depth is generally deep enough to insure that the introduced biosolids will be sequestered, even without thick and clearly defined layers of alternating low permeability, fluid flow barriers and high permeability fluid absorption zones specific, and deep enough to ensure that the introduced biosolids will not pose a potential threat to the environment or to water supplies, and near enough to the surface to allow biosolids introduction in a cost-effective manner. In a particularly preferred embodiment, the introduction formation is between about 500 m and about 3000 m below the ground surface.

The introduction site typically requires less than 10,000 $m^2$ of surface land, unlike the larger areas required for surface landfills. Further, use of the surface land itself according the present method is only temporary, and after the disposal activity is complete, the surface land can be returned to other uses.

The introduction site and introduction formation for use in the present method should be selected to additionally protect ground and ocean waters by properly selecting an appropriate geological interval which does not outcrop or interact with near surface formations. Geochemical analysis of formation fluids can be used to verify that particular introduction formations contain only ancient fluids and are not in communication with shallower water sources.

It is also preferred that the selected introduction formation has pre-existing natural gas because this implies that the introduction formation is overlain by a suitable methane accumulation zone and is capped by an unfractured layer of relatively low permeability so as to inhibit further upward methane movement. This configuration allows for accumulation of gases generated by degradation of the biosolids and removal of the gases for use as a fuel.

It is further preferred that introduction sites selected for use with the present method have existing gas collection and measurement infrastructure, and long histories of contained introduction operations. For example, preferred introduction formations include oil and gas trapping anticlines which over geologic time have proven to be completely isolated.

The overlying low permeability layers, when present, above the preferred introduction formation provide a permeability barrier to upward migration, as can be evidenced by historical oil/water accumulations, where the oil migrates upward until it is impeded by a permeability barrier. The at least one additional overlying high permeability layer acts as a fluid flow sink in the unlikely event of a well casing cement failure or a breach of a low permeability layer.

For example, if the well casing cement fails or a low permeability layer is breached and fluid migrates above the low permeability layer, the high permeability layer immediately above absorbs the excess pressure and migrating fluid. Pressure will then decline slightly in the introduction formation and increase in the overlying layer. These pressure changes and fluid migration can be identified by monitors located in both zones, and periodic wellbore tracer surveys. Further groundward migration of the waste material will not occur unless the second higher high permeability layer also becomes highly pressurized. For material to migrate upwards from the introduction formation, the process of breach and absorption in the layers above the introduction formation would have to be repeated for each set of high permeability and low permeability layers above the introduction formation.

As an example, a suitable underground formation for introduction of biosolids according to the present invention would be a 100 m thick, unconsolidated sandstone formation lying between 1000 m and 3000 m below the ground surface, where the sands are poorly sorted and range in texture from very fine to coarse grained. An approximately 300 m thickness low permeability formation material would be present in the 1,000 m interval immediately above the introduction formation, which are interbedded with high permeability formations providing additional geologic barriers and safety zones and which could be easily monitored.

The introduction formation would have been used as a gas storage field for at least ten years, the geology of the area would be well characterized and injectivity into the introduction formation would have been established. A nearby well would preferably be present which could be used as an observation well for monitoring purposes. Further preferably, there would be no groundwater extraction wells in the area and groundwater would be regularly and extensively monitored.

In another preferred embodiment, the present invention includes creating and maintaining fractures within the selected introduction formation by the introduction of the waste under high pressure, such as parting pressure, as will be understood by those with skill in the art with reference to this disclosure.

After selection of a suitable introduction formation and introduction site, the introduction equipment and associated facilities are located in an area adjacent to the introduction site. Introduction equipment preferably occupies a surface area of 10,000 $m^2$ or less, with no additional surface construction or road work required.

The preferred biosolids introduction apparatuses should be environmentally secure in the handling of waste material. Further preferably, they should be able to screen waste streams on a continuous basis to avoid introduction of any oversize material into the wellbore that could lead to blockage, as well as to monitor and register introduction parameters such as rate, total volumes, pressure, density and temperature in real-time.

Suitable cased and perforated wells are prepared or existing wells modified and extended into the introduction formation, and into the methane accumulation zone if desired. All wells used in the present method are designed to seal against fluid and gas migration and are periodically tested to ensure that migration is not taking place. The capacity for each well is preferably in the range of 500 to 2000 $m^3$ per day of biosolids. By selecting multiple deep introduction targets, and alternating between multiple wells and intervals, a single site can provide large-scale biosolids management capacity for many years.

In a preferred embodiment, each well used in the present invention has several layers of protection. An outer steel casing (called the surface casing) extends from the surface to the lowermost depth of any usable groundwater. This steel casing is surrounded by cement. One or more additional steel casing strings (called the production casing) extends from the surface to the depth of the selected introduction formation. This casing is also surrounded by cement.

The biosolids to be disposed are pumped down a steel tubing past a packer located at an appropriate depth, for example, a depth of about 1,500 m to 2,000 m. Outside the tubing is an annular region filled with fluid. The pressure of this fluid will be constantly monitored to immediately detect any leak in the tubing. If material introduced down the tubing does leak into the annular region, the material is still contained within an outer steel casing, which is in turn surrounded by a cement sheath.

After selection of a suitable introduction formation and preparation of the introduction site, the biosolids are transported to the introduction site. The transport can be by road-based transport. In a preferred embodiment, however, the biosolids are transported by pipe from the source directly to the introduction site, which is located as close to the source of material as practical.

In a preferred embodiment, a biosolids mixture is designed to generate methane efficiently under the conditions present in the selected introduction formation. This is accomplished by measuring the chemical and biological properties of the available biosolids stream, the physical conditions in the target stratum, and adjusting the physical and chemical properties of the biosolids to achieve efficient methane generation.

After the biosolids are introduced into the introduction formation and locked in by the natural stresses present in the introduction formation and the low permeability zones immediately above the introduction formation, the introduced material is allowed to undergo degradation under anaerobic conditions. Given a solids mixture undergoing anaerobic digestion, an estimate of degradation can be obtained from first order kinetics:

$$W = W_0 e^{-kt} \tag{1}$$

where W=mass of volatile introduced solids that have not degraded after time t, $W_0$=mass of solids deposited, k=decay coefficient, and t=time. In general the value of k will depend on a variety of factors including pH, temperature, salinity, mixing amount, and to some extent the concentration of solids. Typical values for the exponent k are on the order of $10^{-3}$, yielding a value for W of between 40–60% degradation per year. For continuous introduction, the amount of material remaining after some time t is determined by integration of equation 1. The mass of gas produced will in general be equal to the amount of volatile introduced solids degraded and is typically composed mainly of methane (50–60%), carbon dioxide (30–40%), nitrogen, and hydrogen.

In addition to the mechanical protection provided by the introduction well design, and the natural protection provided by the selection of an appropriate introduction formation with multiple overlying barrier and buffer zones, the present method preferably includes a continuous real-time recording and display of pressure response in the introduction zone, in the first overlying high permeability zone, as well as in the wellbore annulus, to ensure containment of biosolids in the introduction formation. Any breach or deviation from anticipated introduction behavior will be noted while material is still far below the groundwater, allowing immediate remedial action. Additional process monitoring can include several types such as pressure recording and analysis, temperature recordings, surface deformation measurements and analysis, and microseismic monitoring, such as monitoring pressure in one or more than one of the alternating layers of high permeability and low permeability above the introduction formation during a time selected from the group consisting of before biosolids introduction, during biosolids introduction, after biosolids introduction and a combination of before biosolids introduction, during biosolids introduction and after biosolids introduction, as will be understood by those with skill in the art with reference to this disclosure. The monitoring is preferably performed at several depths below the groundwater base.

Preferably, fluid introduction into the introduction formation is episodic in order to facilitate the monitoring of formation behavior. Bottom-hole pressure in the introduction formation is preferably monitored continuously during daily introduction and nightly shut-in. This pressure information is analyzed to evaluate changing formation flow and mechanical properties and injectivity, and to determine formation parting pressure and material containment, as will be understood by those with skill in the art with reference to this disclosure. Additional biosolids will not be introduced if pressure in the introduction formation remains abnormally high. As will be understood by those with skill in the art, in order for fluid to migrate out of the introduction formation, a breach must occur and the pressure in the introduction formation must be higher than the pressure in an adjacent formation. In addition to the continuous pressure monitoring and analysis, the present method preferably includes shutting down the introduction well periodically to perform extensive well tests, tracer surveys and introduction formation tests to evaluate well integrity and hydraulic isolation in the near wellbore area.

In another preferred embodiment, the present method includes recovering the methane generated from the degradation of the introduced biosolids. The methane can then be used as a clean fuel. Alternatively, the methane produced can be left underground as a stored supply of future energy. Recovery of the methane is preferably done by injecting the biosolids into an appropriate geologic formation with a trapping mechanism. Preferably, the biosolids are introduced downdip below the water-oil or water-gas contact in a geologic formation. The generated methane and carbon dioxide will then migrate upwards due to gravity segregation.

Methane and carbon dioxide produced by the degradation of biosolids according to the present invention will percolate through formation water where much of the carbon dioxide will be sequestered underground by dissolution in the saline formation water, and where the high quality methane will accumulate in the gas trap. The difference in sequestration is due to the much higher solubility of carbon dioxide in water relative to methane (a ratio of at least 10:1) at temperature and pressure conditions typical for deep geologic formations. Methane, in particular, is a potent greenhouse gas. By injecting biosolids into the deep subsurface, gas release to the atmosphere is eliminated and carbon is permanently sequestered in deep saline formations.

Recovered methane from deep introduction formations used according to the present invention is of higher quality than that generated in surface digesters or from surface landfills for two reasons. First, by percolating through formation waters in the introduction formation, the carbon dioxide component of the generated gases will be significantly absorbed due to the much higher solubility of carbon dioxide relative to methane. Second, the methane generated according to the present invention is at higher pressure than methane generated by surface landfills and requires less compression for storage or use.

As can be appreciated, once the introduction formation is filled and the methane extracted, if desired, the equipment used for introduction of biosolids and recovery of methane can be removed and the site abandoned. This returns the surface land to the condition it was in previously and leaves the site unimpaired.

In a preferred embodiment, the present method includes increasing the rate of biodegradation of the introduced biosolids. This is done by altering environmental conditions in the introduction formation or by adding substances or bacteria, or by adjusting the biochemical properties of the biosolids that are introduced into the formation, or by a combination of these actions, to optimize the biodegradation process. In another preferred embodiment, the present method includes decreasing the rate of production of undesirable products such as carbon dioxide, sulfur dioxide and hydrogen sulfide.

For example, the rate of biodegradation can be increased by adjusting the temperature and salinity of the biosolids so that the resulting physical properties of the biosolids in the subsurface provides an optimum environment for biodegradation, given the species of bacteria present in the biosolids and native to the introduction formation. In another preferred embodiment, biodegradation rates can be increased by adding appropriate natural or genetically engineered bacteria to the biosolids prior to introduction, or after introduction. The inoculation can be used to increase the decomposition rate of the biosolids into methane under the specific temperature and pressure conditions at the introduction formation depth, or to inhibit the production of undesirable decomposition products, such as carbon dioxide, sulfur dioxide and hydrogen sulfide. Further, nutrients and other chemical or organic agents, such as those that alter acidity, pH, or oxidation potential, Eh, can be added to the biosolids for the same purposes.

For example, bacteria that are relied upon to promote biodegradation of the introduced biosolids can have high potassium requirements. Extrinsic potassium, such as soluble salt potassium chloride (KCl), can be added to an introduced biosolids to promote bacterial growth.

In general, it is preferred that chemicals added to the introduced biosolids be only weakly soluble in water or insoluble so that any added chemical is not removed during the water expulsion that accompanies compaction of the introduced material in the formation. A suitable source of potassium for addition to the biosolids, therefore, would be finely ground potash feldspar which contains potassium that is slowly liberated in situ under the influence of aqueous exposure, high temperatures and bacterial action.

For example, biodegradation in an introduction formation can be limited by the supply of phosphorous present in one introduced biosolids. In order to improve biodegradation, a second waste stream rich in phosphorous can be blended with the first waste stream or introduced separately, either simultaneously or alternating with the first biosolids. For example, a waste source rich in phosphorous can come from a chemical plant or from phosphorus-rich gypsum wastes ("phospho-gyp").

In another example, some waste streams contain sterile biosolids due to their alkalinity, such as waste streams from paper production facilities. In order to promote bacterial degradation of the wastes, a second waste stream which is acidic can be blended with the first stream to adjust the pH of the streams to promote bacterial degradation of the introduced biosolids.

In yet another example, natural or genetically engineered bacteria can be added to the introduced biosolids to improve degradation. In a preferred embodiment, the bacteria added are anaerobic species because of the low concentration of oxygen in the introduction formations used in the present invention. In a particularly preferred embodiment, the bacteria are methanogenic.

Additionally, a plurality of biosolids having different compositions can be blended together to maximize biosolid degradation in the introduction formation, or to maximize the rate and quantity of methane generation, or to decrease the rate and quantity of generation of less desirable decomposition products such as carbon dioxide, sulfur dioxide or hydrogen sulfide. For example, a source of animal waste that is rich in organic material can be blended with a source of waste materia such as a pulp residue, sawdust from a plywood mill, thermally treated wastes, or other waste that is less rich in organic material, and that is also sterile. The two waste streams are blended in the optimum proportions, as will be understood by those with skill in the art, with reference to knowledge of the in situ conditions at the introduction formation and with reference to this disclosure.

The temperature in the introduction formations used in the present invention can vary from 25° C. (e.g., 1 km deep introduction formation in Montana, US) to 100° C. (3 km deep introduction formation in West-Central California, US). However, suitable thermophilic bacteria can be used with introduction formations having considerably higher temperatures. Pressure also varies at the introduction formation depths anticipated by the present invention, such as from about 10 MPA at a depth of 1 km depth to about 40 MPa at depths of between about 3 to 4 km. Therefore, bacteria added to the biosolids must be chosen to be suitable to the temperature and pressures that will be encountered in a specific introduction formation.

The method for the disposal of biosolids, according to the present invention, therefore, has several advantages over the currently used techniques. First, the present method reduces the potential and real impact on surface waters and groundwater that can be associated with surface application of biosolids, because the biosolids are introduced significantly below any usable source of groundwater. Second, the present method requires significantly less surface land area than land application for disposal of an equivalent volume of biosolids. Third, the present method does not permanently alter the surface land after the disposal at the site is completed. Fourth, because the biosolids can be pumped to local sites for disposal, the present method significantly reduces or eliminates truck traffic to distant disposal sites and, therefore, reduces the noise and environmental contamination associated with heavy truck traffic.

Fifth, the present method reduces the amount of methane and carbon dioxide released into the atmosphere as compared to surface application of biosolids. Sixth, methane produced by the degradation of biosolids according to the present method can be collected for use as an energy source. Seventh, biosolids disposal according to the present method can reduce the cost of biosolids management significantly compared with conventional surface application methods due to the reduced or eliminated need for trucking the biosolids to a distance site for disposal.

Referring now to FIG. 1, there is shown a schematic diagram of one embodiment of the method for the disposal of biosolids according to the present invention. A1 represents the surface facilities (storage, sizing, screening, mixing, blending, process monitoring and pumping equipment) for the formulation of suitable biosolids mixtures for introduction into an introduction formation.

A2 represents the introduction well (or one introduction well in an array of introduction wells) that is cased and cemented in such a manner so as to withstand the introduction pressures implemented over the life of the facility.

A3 represents the introduced biosolids that has been placed and has rapidly, through excess water expulsion, become solidified by the great weight of the overburden rocks. After all the methane possible has been generated by the biodegradation process, A3 becomes a dense and relatively low permeability stratum that is rich in carbon and other organic molecules that were not biodegradable at the conditions in the introduction formation. The sequestered carbon and other organic molecules will not enter the atmosphere creating greenhouse effects.

A4 represents the introduction formation into which the biosolids, A3, was introduced. A4 is of sufficient porosity and permeability as to accommodate the excess biosolids fluids without long-term pressure build-up or interaction with shallow, usable groundwaters. In general, the stratum A4 will be chosen as a laterally continuous stratum of sufficient pore volume and flow path connectivity with adjacent strata to take all the water expelled from the biosolids during the compaction process.

A5 represents the evolution and upward movement path of the methane generated by the biodegradation process. Such movement occurs naturally because the methane is of a specific gravity that is far less than that of any interstitial water, and therefore tends to rise through the porous medium, displacing liquid from the pores.

A6 represents the porous and permeable strata where the methane collects through the upward migration and pore liquid displacement process, and from which strata the generated methane can be extracted for use. This zone, A6, is a "trap" for the evolved methane because of a suitable geological structure, which can be in the form of structural closure with folded beds that form an inverted bowl, as shown, or can be in the form of a change of rock type, not shown, in a combination of the two, or in some other suitable disposition of permeable and low-permeability strata.

A7 represents the rocks overlying the introduction formation that are of sufficiently low permeability that gas cannot flow upward through the pore space. Also, the overlying rocks A7 are non-fractured, or are minimally fractured so that the methane cannot escape to strata of higher elevation.

A8 represents one or more conventional gas wells that extract the methane from the accumulation site A6. The gas wells, A8, either exist at the site before the disposal operation begins or are specifically installed as cased, cemented wells, perforated so that the gas can flow into the wellbore. Depending on the configuration of the strata, the methane extraction wells A8 may be vertical, horizontal or inclined.

A9 represents a surface facility for power generation that can use the extracted methane as a clean energy source. Alternately, the extracted methane can be shipped directly to consumers for home use or industrial users for other purposes.

Although the present invention has been discussed in considerable detail with reference to certain preferred embodiments, other embodiments are possible. For example, the method of the present invention can be applied to the disposal of solids other than biosolids. Therefore, the scope of the appended claims should not be limited to the description of preferred embodiments contained in this disclosure.

What is claimed is:

1. A method for the disposal of biosolids, the method comprising:
   a) providing a supply of biosolids;
   b) selecting an introduction formation below a ground surface, the introduction formation comprising a natural gas formation in a gas accumulation zone;
   c) introducing the biosolids into the introduction formation at a pressure sufficient to create and maintain fractures within the selected introduction formation; and
   d) allowing degradation of the introduced biosolids.

2. The method of claim 1, where the supply of biosolids is derived from at least one source selected from the group consisting of municipal sewage waste, waste water treatment waste, animal waste, non-human-non-animal industrial waste and a combination of the preceding.

3. The method of claim 1, where the introduction formation is at least about 100 meters below the ground surface.

4. The method of claim 1, where the introduction formation is from between about 500 and about 3,000 meters below the ground surface.

5. The method of claim 1, where the introduction formation has a temperature and the temperature of the introduction formation is greater that about 25° C.

6. The method of claim 1, where the introduction formation has a porosity greater than about 15%.

7. The method of claim 1, where the introduction formation is separated from the ground surface by one or more pairs of alternating layers of high permeability and low permeability.

8. The method of claim 7, further comprising monitoring pressure in the one or more than one of the alternating layers of high permeability and low permeability above the introduction formation during a time selected from the group consisting of before biosolids introduction, during biosolids introduction, after biosolids introduction and a combination of before biosolids introduction, during biosolids introduction and after biosolids introduction.

9. The method of claim 7, where at least one low permeability layer of the one or more alternating layers of high permeability and low permeability comprises shale.

10. The method of claim 7, where the one or more pairs of alternating layers of high permeability and low permeability is at least three pairs of alternating layers of high permeability and low permeability.

11. The method of claim 1, where allowing degradation of the biosolids generates a gas selected from the group consisting of carbon dioxide, sulfur dioxide, hydrogen sulfide and combinations of the preceding.

12. The method of claim 11, further comprising decreasing the rate of the generated carbon dioxide, sulfur dioxide, hydrogen sulfide or combination of the preceding by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding.

13. The method of claim 1, further comprising transporting the selected biosolids to an introduction site by pipe before injecting the biosolids.

14. The method of claim 1, further comprising monitoring pressure in the introduction formation at a time selected from the group consisting of before injecting the biosolids into the introduction formation, during the introduction of the biosolids into the introduction formation, after injecting the biosolids into the introduction formation and a combination of the preceding.

15. The method of claim 1, further comprising increasing the rate of degradation of the biosolids by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding.

16. The method of claim 15, where the chemical added to the biosolids is potassium.

17. The method of claim 1, further comprising allowing methane to be generated by the degradation of the introduced biosolids and recovering methane generated by the degradation of the introduced biosolids, after injecting the biosolids into the introduction formation.

18. The method of claim 17, further comprising increasing the rate of methane generation by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding.

19. The method of claim 18, where the chemical added to the biosolids is potassium.

20. The method of claim 1, where the degradation of the biosolids generates a gas selected from the group consisting of carbon dioxide, sulfur dioxide, hydrogen sulfide and combinations of the preceding, and where the method further comprises decreasing the rate of the generated carbon dioxide, sulfur dioxide, hydrogen sulfide or combination of the preceding by performing an action selected from the group consisting of blending at least one waste stream with the provided biosolids, inoculating the biosolids with at least one species of bacteria, changing the temperature of the biosolids, changing the salinity of the biosolids, adding at least one chemical to the biosolids and a combination of the preceding.

21. The method of claim 20, where the chemical added to the biosolids is potassium.

* * * * *